United States Patent [19]

Lindsay

[11] Patent Number: 4,868,396
[45] Date of Patent: Sep. 19, 1989

[54] CELL AND SUBSTRATE FOR ELECTROCHEMICAL STM STUDIES

[75] Inventor: Stuart M. Lindsay, Tempe, Ariz.

[73] Assignee: Arizona Board of Regents, Arizona State University, Tempe, Ariz.

[21] Appl. No.: 108,156

[22] Filed: Oct. 13, 1987

[51] Int. Cl.⁴ .............................................. G21K 5/08
[52] U.S. Cl. .............................. 250/440.1; 250/442.1; 250/306
[58] Field of Search .................. 250/440.1, 442.1, 306, 250/307

[56] References Cited

U.S. PATENT DOCUMENTS 4,668,865  5/1987  Gimzewski et al. ................ 250/306

OTHER PUBLICATIONS

Sonnenfeld, Richard et al, "Atomic-Resolution Microscopy in Water", *Science*, vol. 232, Apr. 1986, pp. 211-213.

Travaglini et al, *Surface Science*, vol. 181, 1987, pp. 380-390.

*Primary Examiner*—Bruce C. Anderson
*Assistant Examiner*—John A. Miller
*Attorney, Agent, or Firm*—Richard R. Mybeck

[57] ABSTRACT

A cell and substrate for use with a scanning tunneling microscope to image molecules adsorbed on a noble metal surface disposed under solvent in conducting electrochemical studies and methods for preparing atomically flat metal surfaces as the substrates for the STM and for plating molecules onto the metal substrate for examination.

20 Claims, 4 Drawing Sheets

CELL AND SUBSTRATE FOR ELECTROCHEMICAL STM STUDIES

INTRODUCTION

The present invention relates to a cell and substrates for electrochemical scanning tunneling microscope ("STM") studies and more particularly to a novel cell and substrate system for use with a STM to image molecules adsorbed on a metal surface disposed under solvents such as water.

BACKGROUND OF THE INVENTION

Despite the enormous advances in imaging of biopolymers by conventional electron microscopy (see: Fujiyoshi et al, *Ultramicroscopy*, 7, 189–192, 1981) and by STM in air (see: Travaglini et al, *Surface Science*, 181, 380–390, 1987), the ability to image in an aqueous environment offers certain advantages not yet fully realized. While a graphite surface with atomic resolution has been observed using an STM in water (see: Sonnenfeld et al, *Science*, 232, 211–213, 1986), a need still exists for obtaining atomic resolution of adsorbate molecules in such an environment, and it is toward the creation of reproducible images which outline the overall shape of the molecules in such an environment that the present invention is directed.

BRIEF SUMMARY OF THE INVENTION

The present invention provides easily operated reliable means and methods for imaging molecules adsorbed on a metal surface disposed under solvent with an STM. More particularly the present invention advances the art by the development of a stable microscope, a unique substrate and sample cell for use therewith, a special buffer salt solution for use therein, and plating methods especially suited for depositing molecules on the substrate.

Accordingly, a principal object of the present invention is to provide an improved cell and substrate for use with an STM to image molecules adsorbed on a metal surface disposed under a solvent such as water.

Another object of the present invention is to provide improved means and methods for creating reproducible images outlining the overall shapes of molecules with an STM.

A further object of the present invention is to provide a special buffer salt solution for use with an STM to create reproducible images of molecules therewith.

Still another object of the present invention is to provide unique plating methods for depositing molecules onto the metal substrate.

A still further object of the present invention is the provision of a novel and unique substrate for use in an STM.

These and still further objects as shall hereinafter appear are readily fulfilled by the present invention in a remarkably unexpected fashion as will be readily discerned from the following detailed description of the preferred embodiments thereof, especially when read in conjunction with the accompanying drawing in which like parts bear like indicia throughout the several views.

THE DRAWINGS

In the drawings:

FIG. 1b shows a plan view of the cell of FIG. 1a.

DESCRIPTION OF PREFERRED EMBODIMENTS

Figure 1A:
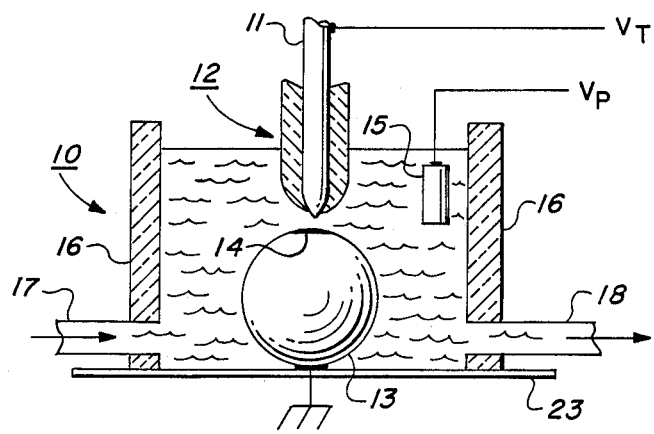
FIG. 1a is the layout of an STM electrochemistry cell embodying the present invention.

Referring to FIG. 1a in which the STM electrochemistry cell is identified by the general reference 10, each unit includes a platinum tip 11, glass insulation 12, a ball 13 formed of gold, platinum or like noble metal having flat facets 14, a plating electrode 15, glass walls 16, an inlet tube 17 and an outlet tube 18, the function and structure of which shall now be described.

THE MICROSCOPE, CELL AND SUBSTRATE

The microscope is a small instrument based on lead-zirconium-titanium "PZT" rings (which are more rigid than tubes). The xy scanning is achieved with a push-pull motion using a cruciform made from four such rings. The sample to be measured is advanced towards the tip with an "Inchworm" PZT walker which works through a 20:1 reduction lever pushing on a deformable drum that holds the sample. Constraints on the sample stage and tip are radially symmetric to minimize drift in the xy plane. The structure is re-entrant and compensated in the z direction. Atomic resolution is routinely obtained on "easy" smaples such as graphite. A complete description of a microscope suitable for use herewith appears in my copending U.S. patent application Ser. No. 108157, filed 10/13/87.

While the initial work herewith employed a dropper to dispose a sample under the tip 11, it has been found that the use of a small cell (~50 μl volume) instead, greatly reduces problems caused by evaporation. Tip 11 is partially insulated with glass 12 which reduces the conduction current to around 0.1 nA with the tip at 100 mV in a typical electrolyte. The substrate is small noble metal ball 13 made by melting gold, platinum or like noble metal wire with a gas torch. Ball 13 has facets 14 which are much flatter than evaporated gold surfaces. A plating electrode 15 (herein "P.E.") made of a chemically inert metal such as platinum or gold is immersed in the cell which is bounded by perimeter glass walls 16. As shown in FIG. 1a, an inlet 17 and an outlet 18 are provided for ingress and egress of the electrolyte.

Figure 1B:
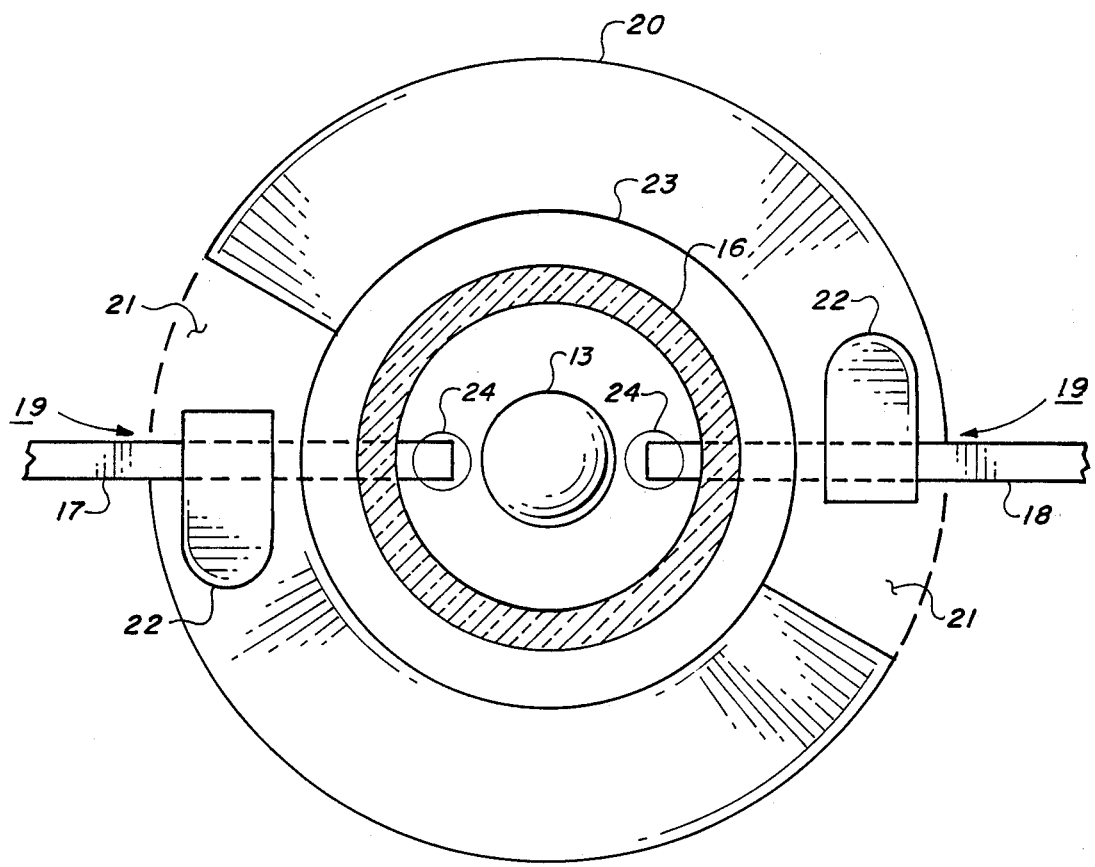

As shown in FIG. 1b, the ingress 17 and egress 18 tubes also serve as pins in a bayonet fitting 19 which rigidly secured the cell on the STM sample stage while also permitting easy removal and replacement of the cell for cleaning. The tubes 17 and 18 push into notches 21 in a retaining ring 20 and the cell is rotated so that the spring clips 22 hold the tubes 17 and 18 in place. The tubes 17, 18 are fitted into the stainless steel base 23 of cell 10, and holes 24 allow the electrolyte to be injected into or removed from the cell 10.

The noble metal ball 13 is used because it can be prepared so as to have atomically flat facets 14 which form deal substrates for the STM. The preparation of gold and platinum balls with automatically flat facets by melting wire and quenching in air is described in the literature for other purposes (see: T. Hsu and J. M. Cowley, *Ultramicroscopy* 11, 239–250 (1983)). The wire is melted in a propane-oxygen flane to form a small ball of about 1 mm diameter. Inspection of the surface under an optical microscope reveals numerous small (a few microns) facets. The ball is mounted in the cell either with adhesive or by locking the wire into a hole formed in the base 23 of cell 10. A ball is chosen with a facet near its top so that the STM tip may be adjusted to be over the facet.

In use, the tip leakage was ohmic at biases less than 500 mV, and such biases did not appear to alter the images with repeated scanning. The images shown in the drawing were taken with a Pt tip operated at $-100$ mV with a tnnel current of 1 nA.

THE MECHANISM OF STM IN AIR AND WATER

Tunnel current-distance (I—s) characteristics shown in the drawing were obtained by slowly scanning (2 Hz) the tip-substrate substrate separation and recording the logarithm of $1_t$ on a digital storage oscilloscope. The PZTs were calibrated both by using the STM head to scan a small Fabry-Perot mirror and by scanning graphite. Both methods gave results which agreed with the manufacturer's specification within 10%. Evaporated gold substrates and both platinum and tungsten tips were used.

Figure 2:
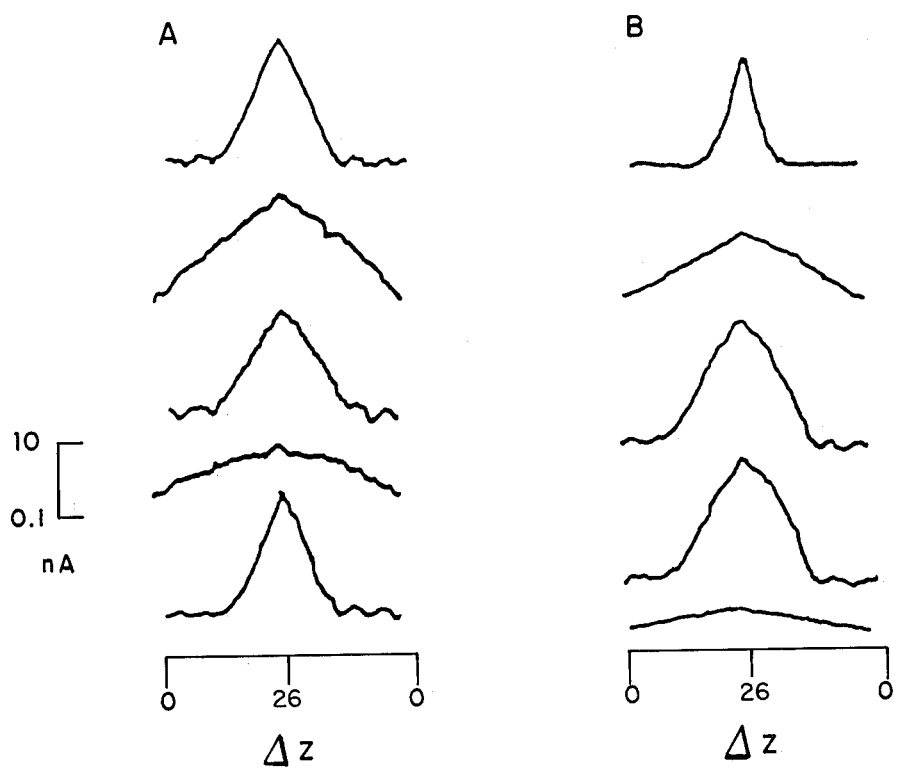
FIG. 2 shows tunnel current-distance curves taken in air (A) and water (B)

A selection of traces from among several hundred taken in both 18 M $\Omega$ water and air are shown in FIG. 2. The traces are characteristic of tunneling, showing little hysteresis. The tip was scanned back and forth from the gold substrate over adistance of 26A with the closest approach at the center of the scan. The current scale is logarithmic, but the traces have been arbitrarily displaced vertically for clarity. The curves go flat at the lowest value of current measured (0.05 nA) as the tunnel current falls below the amplifier noise. These curves were selected as representative of several hundred recorded at different locations over the surface.

When fitted to the Simmons formula (see: Simmons, *J. Applied PHysics*, 34, 1793–1803; 1963) using 1.025 eV$^{-\frac{1}{2}}$A$^{-1}$ for the constant in the exponent, the data yield values for the "barrier heights", $\phi$, between about 1 eV and 1 meV, independent of the medium or tip metals used. The values vary wildly from point to point over the surface. Over typical "clean" areas the value is about 0.5 eV. Over what appear to be patches of adsorbate, the values can fall dramatically. The distribution of effective barrier heights is monitored by mapping $dI_t/ds$ by modulating the z PZT rapidly and measuring the in-phase ac component in $I_t$ with a lock-in amplifier (images are acquired simultaneously with topology maps). A typical result over a "dirty" gold surface is shown in FIG. 3 (this image is obtained in air, but very similar results are obtained in water). The surface is flat to within about 40Å over a 1000Å square area. The background value of $dI_t/ds$ corresponds to $\sim 0.5$ eV, falling to meV over an apparent adsorbate patch.

Figure 3A:
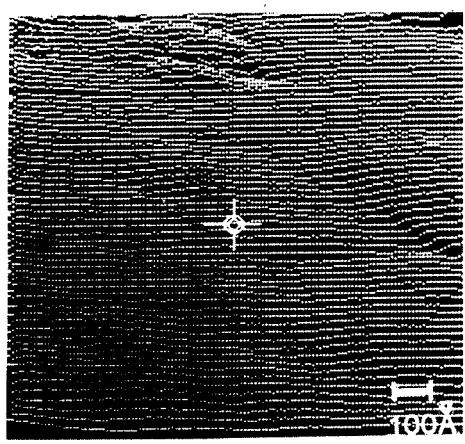
FIG. 3 shows y-modulated topology (A) and a $dI_t/ds$ map (B) for a "dirty" gold surface.
Figure 3B:
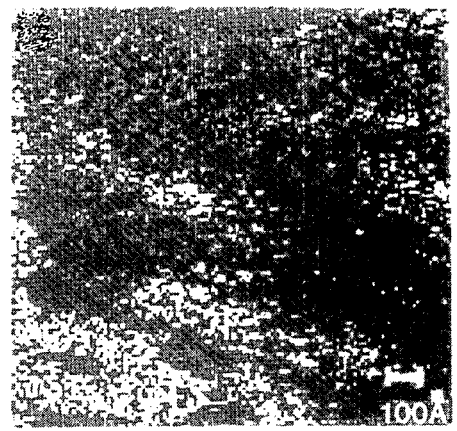

FIG. 3A shows a y-modulated topology map and FIG. 3B shows a $dI_t/ds$ map. The background in 3B corresponds to $\phi \sim 0.5$ eV while the noisy patches in the lower left of the image correspond to areas where $\phi$ falls as low as $\sim 1$ meV. Note that noisy patches also occur in the topology traces where the low $\phi$ patches occur in the $dI_t/ds$ map.

Overall, $\phi$ values are about an order of magnitude lower than vacuum values, falling much lower over what appear to be dirty patches on the surface. Such anomalously low barrier heights are almost certainly an indication of substrate-tip contact via an insulating adsorbate. The models of Coombs and Pethica (see: *IBM J. Res. Develop*, 30, 455–459; 1986) and Mamin et al (see: *Phys. Rev. B.*, 34, 9015–9018; 1986) implicate shear deformation of the substrate as the "weak link"; however such deformation would be rather delocalized, and it is hard to see how such an elastic deformation emchanism could give high reslution. The very rapid variations seen in the $dI_t dS$ map imply some local elastic sensitivity which may arise from a small patch of insulating, deformable adsorbate on the tip. Any asymmetry in such an adsorbate would also account for the hysteresis seen in comparing right-left scans with left-right scans (the usual asymmetry appears mostly as a small systematic displacement in z as oppsed to the small xy displacements caused by possible PZT hysteresis). Images with large ($>5\%$) hysteresis were rejected as they appear to be associated with gross contamination of the tip, and often produced direction-dependent images. The tip is scanned at constant velocity, but only one direction of scan is displayed to remove any "interference" caused by the residual hysteresis. However, left-right and right-left images viewed side by side do not look substantially different.

Contact via insulating adsorbates is believed to explain why the operation of the STM does not appear to depend on the medium (at least in air, water and dirty vacuum conditions). However it does indicate that to be imaged, an adsorbate molecule must be firmly embedded in the surrounding adsorbate. One new mechanism for contrast is as follows: A relatively hard molecule in the adsorbate will cause the z PZT to push forward to maintain $I_t$, while a relatively soft molecule will cause the z PZT to pull back.

IN-SITU PLATING AND THE CHOICE OF BUFFER SOLUTIONS

Figure 4A:
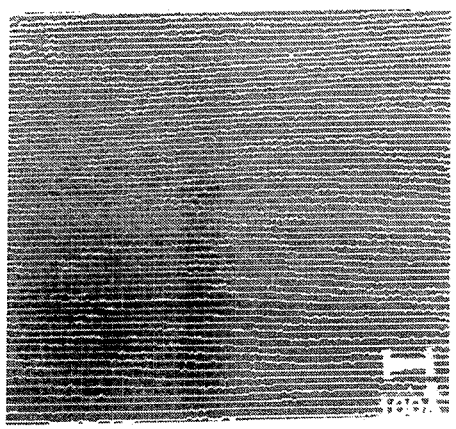
FIG. 4 illustrates the plating procedure of the present invention with and without DNA in the buffer.
Figure 4B:
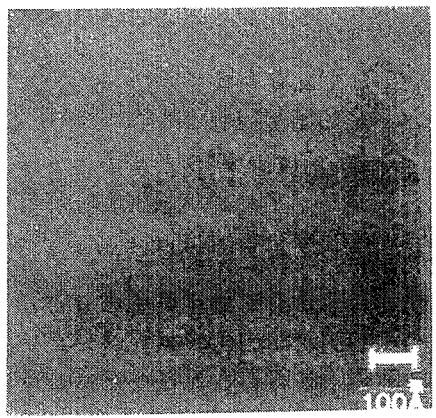
Figure 4C:
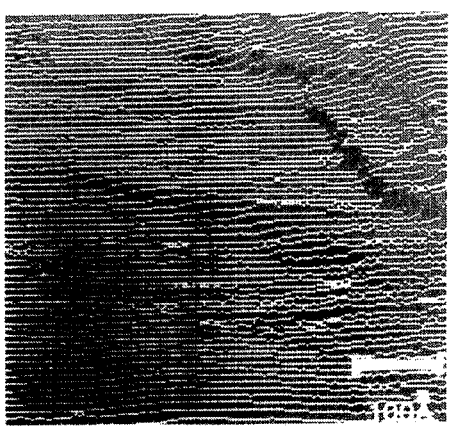

A buffer salt is required to maintain pH in the cell, both for electrochemistry to be carried out, and to maintain the conformation of biomolecules in the solution. Heavy organic salts caused "dirty patches" all over the surface in a $dI_t/ds$ image (although the corresponding changes in the y-modulated trace were very easy to distinguish from changes caused by adsorption of large biomolecules). This problem did not arise with $Na_2HPO_2$-$NaH_2PO_4$ buffer. Prolonged application of a plating potential to the PE produced no change in the $dI_t/ds$ maps, although what appear to be microcrystals do eventually grow on the surface. This process is illustrated in FIGS. 4A, 4B and 4C. The surface topology (4A) of a facet is flat apart from 3A steps between terraces; no contamination is evident oin the $dI_t/ds$ map (4B). After prolonged plating, new features appear on the surface (4C). The corresponding $dI_t/ds$ map did not show any features.

FIG. 4 further illustrates a series of experiments which demonstrate the plating procedure of the present invention, with and without DNA in the buffer. As noted above, FIG. 4A shows a y-modulated map of a flat, clean gold facet, showing 3Å steps; FIG. 4B shows a $dI_t/ds$ map of the same rear with no adsorbate patches; and FIG. 4C shows a clean facet after plating is phosphate buffer. The steps are a little of 5Å height each. In addition, FIGS. 4D, 4E and 4F show grayscale, y-modulated topology and $dI_t/ds$ maps taken as the surface is plated with DNA octamer. The PE was turned on at the lower arrow and off at the upper arrow.

Most of the electrochemistry literature on DNA is concerned with adsorption at negative surfaces. Irreversible adsorption occurs by backbonding to the $\pi$ orbitals of the bases. Consequently the DNA is unwound. Since the DNA itself is a negative polyion (partially compensated by condesation), high concentrations are needed for plating at a negative surface.

Figure 4D:
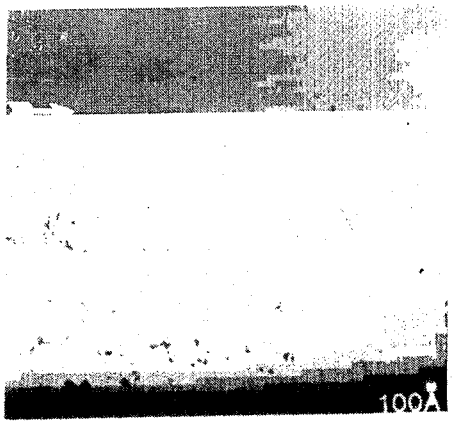
Figure 4E:
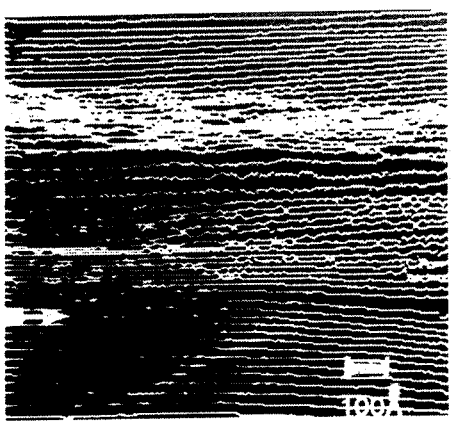
Figure 4F:
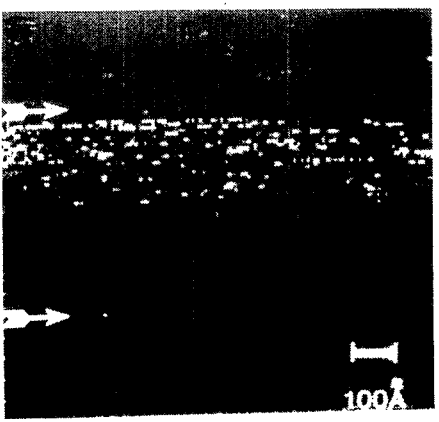
Figure 5A:
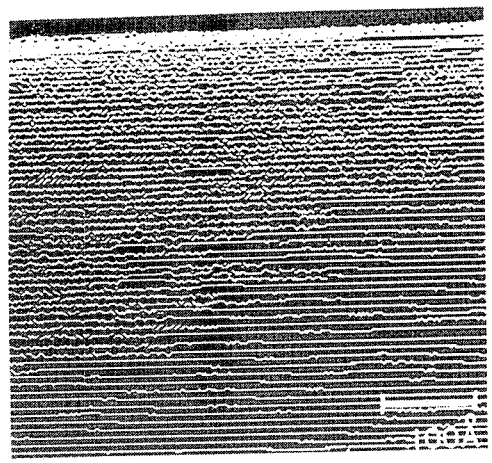
FIG. 5 shows a stable adsorbate patch after plating using DNA octamer.
Figure 5B:
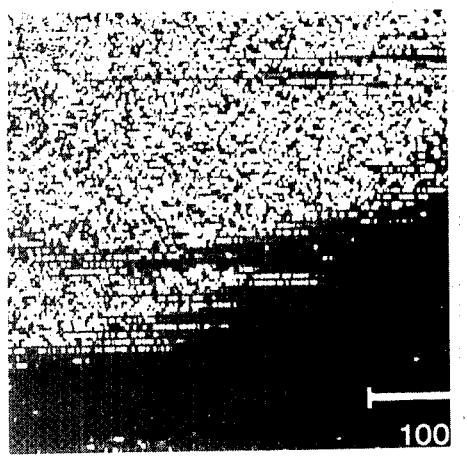

It was found that the aggregates of DNA always formed on the positive electrods when potential differences between the plating electrode and substrate in excess of about 1.5V were applied. Such depositions were monitored directly in the STM during scanning. Deposition is seen soon after the PE is biased, and generally disappears as soon as the PE is returned to zero volts. An example of this process is shown in FIGS. 4D, 4E and 4F which show grey scale, y-modulated and $dI_t/ds$ images of plating during scanning. The sample in this case was a synthetic DNA octamer (d(CGGATCCG) from New England Biolabs). It was dissolved in 50 mM phosphate buffer to 30 μg/mL concentration. As mentioned earlier, this buffer produces no change in the apparent surface topology or $dI_t/ds$ during brief plating cycles. With the DNA in the solution, dramatic changes are seen. The scan was upwards in the experiments shown here, and the plating electrode ("PE") was turned to $-2V$ at the point marked by the lower arrow, and back to 0V at the point marked by the upper arrow. The gray-scale map in FIG. 4D shows a build up to about 90Å over the background level until the PE is turned off. Little detail is seen in the y-modulated image (see: FIG. 4E) as the adsorbate appears to pile up. Large changes in $dI_t/ds$ occur over the heavily plated area (Shown in FIG. 4F). While the plating is generally reversible, many regions of the surface remain coated with aggregates which appear to be quite stable, yielding images hours after the original plating cycle. It is not known why this occurs. There is, however, no discernible correlation between the location of these patches and the underlying topology of the gold surface. The edge of such a patch is shown in FIG. 5 (A-topology, B, $dI_t/ds$). As shown in FIG. 5A, the trace dips down a few Å when the tip is over the DNA. This is in contrast to other organic adsorbates studied, in which the tip may move up or down. Every image taken using DNA shows this behavior when various DNA's and RNA'3 s were tested. It is surmised that this effect indicates that these molecules are generally stiffer than the surrounding adsorbate. Note how well the borders of the patch images in 5A and 5B correlate. Where a small cluster (or even perhaps an isolated molecule) occurs, there is some evidence that the tip may move the adsorbate. This does not appear to be a problem, however, when using higher molecular weight samples.

STRUCTURE IN STABLE AGGREGATES

Aggregates made from high molecular weight material generally show structure. The samples used in the images shown here were made by sonicating high molecular weight calf-thymus DNA. The sonicated material showed a quite sharp band on an agarose gel corresponding to a length of about 400 base-pairs. The sonication, however, probably produces very smal fragments which are not seen on such a gel. The sample was chloroform and phenol extracted until essentially protein-free ($A_{260}/A_{280} \sim 2$). A solution of 100 μg/mL was prepared in 50 mM phosphate buffer.

Figure 6A:
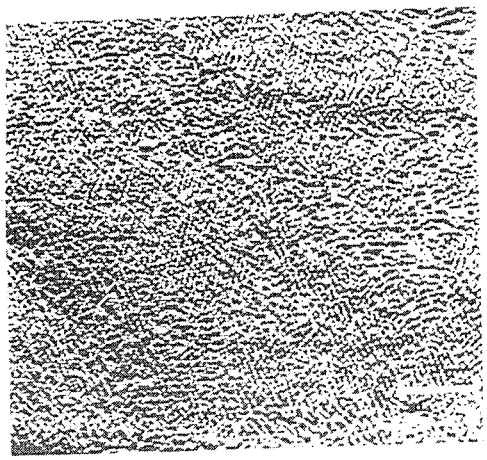
FIG. 6 shows low (A) and high (B) magnification scans over a stable adsorbate patch made using high molecular weight DNA.
Figure 6B:
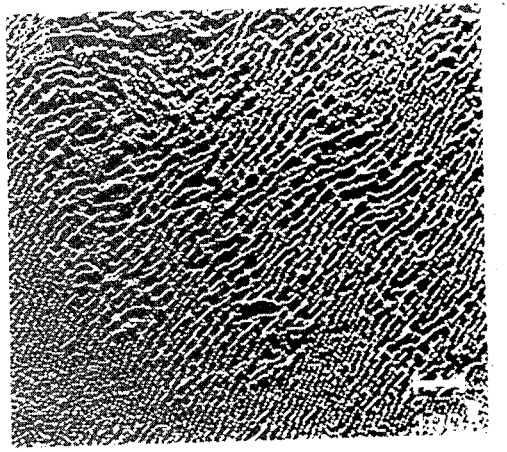

A y-modulated scan over a large stable coated region (3000Å square) is shown in FIG. 6A. Careful inspection reveals a texture. A higher magnification scan over such a patch reveals local liquid-crystal-like order as shown in FIG. 6B. Where the aggregate is close-packed, the corrugation perpendicular to the long axis is always 20Å. This is the diameter of double-helical DNA.

Figure 7A:
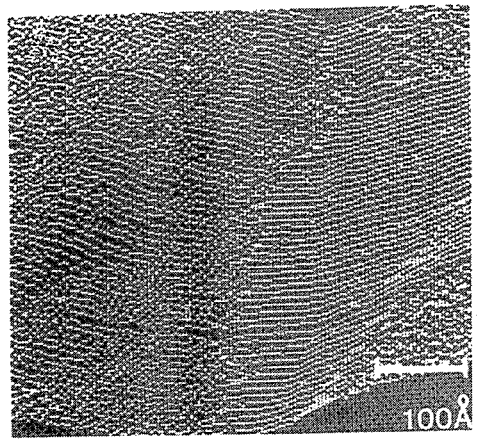
FIG. 7 shows a y-modulated topology (A) and a $dI_t/ds$ map (B) over the edge of a patch of lower molecular weight adsorbate in which is embedded at least one high molecular weight fragment.
Figure 7B:

Occasionally it is possible to locate what appear to be intact strands embedded in a region of otherwise small fragments as shown in FIG. 7. A partially intact molecular may be lying along the edge of the adsorbate batch that runs down the center of the picture (the ends are marked with arrows). It is apparent as the dark streak in the $dI_t/ds$ map (see: FIG. 7B) and clearest in the y-modulated image (see FIG. 7A) at the top of the image, where is appears as a small "trench" in the scan about 20Å wide and a few Å deep.

Thus, a method for producing stable adsorbate patches of DNA and like materials on a metal surface under a buffer solution for imaging by the STM has been described which has worked with all of the charged biopolymers examined. Images representing the overall molecular layout in ordered arrays has been demonstrated. It is believed that the image formation mechanism herein described, which involves mechanical contact between the tip and substrate, explains the medium-independence of the STM operation and will ultimately permit the examination of isolated molecules.

From the foregoing, it is readily apparent that cell and substrate for electrochemical STM studies have been herein described and illustrated which fulfill all of the aforestated objectives in a remarkably unexpected fashion. It is of course understood that such modifications, alterations and adaptations as may readily occur to the artisan skilled in the field to which this invention pertains when confronted with this specification, are intended within the spirit of the present invention which is limited only by the scope of the claims appended hereto.

Accordingly, what is claimed is:

1. A cell and a substrate for use with an electrochemical scanning tunneling microscope having a plating electrode and a scanning tip depending therefrom comprising: a cell member having a bottom surface and a glass perimeter wall extending upwardly therefrom thereabout; an inlet tube extending into said cell; an outlet tube extending from said cell in spaced relationship to said inlet tube; a retaining ring disposed on said bottom surface of said cell intermediate said inlet tube and said outlet tube; and a generally spherical substrate formed on a noble metal and having at least one flat facet thereupon, said substrate being seated on said retaining ring with said flat facet facing said scanning tip in operative relationship thereto.

2. A cell and substrate according to claim 1 in which said cell contains sufficient solvent to submerge said substrate.

3. A cell and substrate according to claim 2 in which said solvent is water.

4. A cell and substrate according to claim 1 in which said substrate is formed of gold.

5. A cell and substrate according to claim 1 in which said substrate is formed of platinum.

6. A cell and substrate according to claim 2 in which said substrate is formed of gold.

7. A cell and substrate according to claim 2 in which said substrate is formed of platinum.

8. A cell and substrate according to claim 1 in which said retaining ring has a plurality of notches defined in the perimeter thereof, a spring clip associated with one of said notches and coacting therewith to secure said inlet tube thereto, and a spring clip associated with another of said notches and coacting therewith to secure said outlet tube thereto.

9. A cell and substrate according to claim 1 in which said bottom surface of said cell member is formed of stainless steel.

10. A cell and substrate according to claim 8 in which said cell contains sufficient solvent to submerge said substrate.

11. A cell and substrate according to claim 10 in which said solvent is water.

12. A cell and substrate according to claim 10 in which said substrate is formed of gold.

13. A cell and substrate according to claim 10 in which said substrate is formed of platinum.

14. A cell and substrate according to claim 9 in which said cell contains sufficient solvent to submerge said substrate.

15. A cell and substrate according to claim 14 in which said solvent is water.

16. A cell and substrate according to claim 14 in which said substrate is formed of gold.

17. A cell and substrate according to claim 14 in which said substrate is formed of platinum.

18. A cell and substrate according to claim 3 in which said substrate is formed of gold.

19. A cell and substrate according to claim 3 in which said substrate is formed of platinum.

20. A cell and substrate according to claim 1 in which an insulating adsorbate layer is operatively interposed in engaging relationship between said tip and said substrate

* * * * *